United States Patent
Kuyama et al.

(10) Patent No.: US 7,892,846 B2
(45) Date of Patent: Feb. 22, 2011

(54) PHOSPHOPEPTIDE ANALYSIS METHOD

(75) Inventors: Hiroki Kuyama, Kyoto (JP); Kazuhiro Sonomura, Kyoto (JP); Osamu Nishimura, Kawanishi (JP)

(73) Assignee: Shimadzu Corporation, Kyoto (JP)

(*) Notice: Subject to any disclaimer, the term of this patent is extended or adjusted under 35 U.S.C. 154(b) by 0 days.

(21) Appl. No.: 12/269,336

(22) Filed: Nov. 12, 2008

(65) Prior Publication Data

US 2009/0137052 A1 May 28, 2009

(30) Foreign Application Priority Data

Nov. 13, 2007 (JP) .............................. 2007-293809

(51) Int. Cl.
*G01N 33/00* (2006.01)
(52) U.S. Cl. ..................... 436/86; 436/103; 436/173
(58) Field of Classification Search ....................... None
See application file for complete search history.

(56) References Cited

U.S. PATENT DOCUMENTS 7,102,005 B2 * 9/2006 Agnew et al. ............... 544/287

OTHER PUBLICATIONS

Sven Kjellstrom, et al., "Phosphoric Acid as a Matrix Additive for MALDI MS Analysis of Phosphopeptides and Phosphoproteins", Analytical Chemistry, 2004, pp. 5109-5117, vol. 76.

* cited by examiner

*Primary Examiner*—Yelena G Gakh
*Assistant Examiner*—David Weisz
(74) *Attorney, Agent, or Firm*—Sughrue Mion, PLLC

(57) ABSTRACT

According to the present invention, a matrix reagent prepared by adding methylenediphosphonic acid (MDPNA) having two phosphonic acid groups as an additive to a matrix of 2,5-dihydroxybenzoic acid (DHBA) is used for the preparation of a sample. By using the sample according to the present invention, it is possible to achieve a higher peak intensity of phosphopeptide as compared with a sample in which DHBA is solely used as a matrix without using an additive, or a sample in which phosphoric acid (PA) is used as an additive in addition to DHBA. Further, use of the sample according to the present invention enables the detection of peptides that cannot be detected in a case of the phosphoric acid-added sample.

5 Claims, 5 Drawing Sheets

PHOSPHOPEPTIDE ANALYSIS METHOD

The present invention relates to a method for analyzing phosphopeptide in biological or other kinds of samples by using a matrix assisted laser desorption ionization mass spectrometer (MALDI).

BACKGROUND OF THE INVENTION

Protein phosphorylation is known to be involved in the regulation of various in-vivo cell functions such as signal transmission, differentiation and proliferation. In recent years, a mass spectrometer, particularly a MALDI mass spectrometer, has been utilized as an effective tool for analyzing phosphorylated sites in proteins in a living organism. However, an analysis using a mass spectrometer of this kind has a problem that, since the ionization efficiency of phosphopeptide is low, and the strength of the ions derived from phosphopeptide is suppressed by a relatively large amount of non-phosphopeptide, the highly-sensitive detection of phosphopeptide is difficult.

In order to solve this problem, research and development has been carried out in various places mainly on the following three aspects:

(i) specific enrichment of phosphopeptide;
(ii) desorption and chemical modification of the phosphate group of phosphopeptide; and
(iii) selection of a matrix or a matrix additive for sample preparation.

The methods (i) and (ii) out of the three methods have a problem that the highly sensitive detection of phosphopeptide is not assuredly achieved even though the processes and operations are complex and cumbersome. On the other hand, the method (iii) does not require a special process or operation unlike the methods (i) and (ii), and thus the method (iii) can be said to be the most convenient method, with which the analysis throughput is easily improved.

As a conventional technique for the method (iii), a non-patent document "Phosphoric Acid as a Matrix Additive for MALDI MS Analysis of Phosphopeptide and Phosphoproteins" (Sven Kjellstrom et al. *Analytical Chemistry*, 2004, 76, pp. 5109-5117) discloses that the phosphopeptide-detection efficiency can be improved by using 2,5-dihydroxybenzoic acid (DHBA) as a matrix and adding a phosphoric acid in a sample solution during the preparation of the sample.

Although application of the conventional method improves the phosphopeptide-detection efficiency to some extent, the extent of the improvement is insufficient. Moreover, results of a test conducted by the present inventors revealed that, when a phosphoric acid is used as a matrix additive, some peptides were not easily ionized and specific kinds of non-phosphopeptide were almost not at all detected. Accordingly, the presence of undetectable peptides itself causes a significant problem, and further leads to a lower sequence coverage in protein identification by, in particular, peptide mass fingerprinting (PMF). Hence, credibility of the test result may be greatly deteriorated.

SUMMARY OF THE INVENTION

To solve the aforementioned problems, the present invention intends to provide a method for analyzing phosphopeptide capable of detecting phosphopeptide with higher sensitivity as compared with conventional methods.

Another purpose of the present invention is to provide a method for analyzing phosphopeptide capable of unexceptionally detecting any non-phosphopeptide as well as phosphopeptide, thereby increasing the credibility of protein identification by for example PMF.

The present inventors have repeatedly performed tests on various compounds concerning sensitivity for detecting phosphopeptide and non-phosphopeptide, sensitivity for detecting alkali metal-adduct ions that make background noise in a mass spectrum, and other items, and also to find a matrix additive to be replaced with the conventionally used phosphoric acid. As a result, they finally found that a compound containing a phosphonic acid group creates a good result, and thereby completed the present invention.

Namely, the present invention to solve the aforementioned problem is a method for analyzing phosphopeptide by using a matrix assisted laser desorption ionization (MALDI) mass spectrometer, characterized by using a matrix to which a compound containing a phosphonic acid group is added in the preparation of the sample.

As a matrix to be used in the method for analyzing phosphopeptide according to the present invention, it is possible to use 2,5-dihydroxybenzoic acid (DHBA) that is easily obtainable and widely used conventionally.

Examples of the compound containing one phosphonic acid group include a phosphonic acid, a methylphosphonic acid, a phenyl phosphonic acid, a 1-naphtylmethyl phosphonic acid, and other compounds. Examples of the compound containing two phosphonic acid groups include a methylenediphosphonic acid, an ethylenediphosphonic acid, an ethane-1-hydroxy-1,1-diphosphonic acid, a nitrilotriphosphonic acid, an ethylenediaminetetraphosphonic acid, and other compounds.

Use of an aforementioned kind of compound containing two or more phosphonic acid groups, preferably two to four phosphonic acid groups in one molecule as an additive is especially effective for improving the sensitivity for detecting phosphopeptide. The effect for improving the sensitivity for detecting phosphopeptide can be exerted in both positive ionization and negative ionization.

According to one of the preferable embodiments of the present invention, the compound containing phosphonic acid groups is methylenediphosphonic acid.

The method for adding the compound containing phosphonic acid groups to a matrix may be achieved when the compound containing phosphonic acid groups and a matrix are made to coexist on a sample plate that is used for setting a subject sample in the MALDI mass spectrometer. The method may also be achieved by previously preparing a sample solution containing phosphopeptide, a matrix additive solution containing the compound containing phosphonic acid groups, and a matrix solution containing a matrix, and then individually dropping each of the solutions on a sample plate. In this case, the order of dropping the solutions is not fixed. Further, the method may be achieved by previously preparing a solution containing both a compound containing phosphonic acid groups and a matrix, and then dropping the solution containing both a compound containing phosphonic acid groups and a matrix on a sample plate before or after the dropping of a sample solution.

A solvent used for preparing the matrix additive solution or the matrix solution may be appropriately selected from the group consisting of an acetonitrile solution, a trifluoroacetic acid (TFA) solution, an acetonitrile-trifluoroacetic acid (TFA) solution, and other solutions. The content of the matrix additive in the matrix additive solution may be approximately 0.01% (w/v) or more, and more preferably, approximately in the range from 1 to 5% (w/v) in view of the phosphopeptide-detection sensitivity. The content of the matrix in the matrix solution is not particularly limited, and for example the matrix solution may contain the matrix at a concentration of 1% to saturation.

It is to be noted that the phosphopeptide as a test object in the analysis method according to the present invention include not only phosphopeptide but phosphoproteins as well. The phosphoproteins may be fragmented by a known method to be provided as a mixture of phosphopeptide and non-phosphopeptide, and then the mixture is used as a sample for the analysis method according to the present invention.

The method for analyzing phosphopeptide according to the present invention makes it possible to detect phosphopeptide with higher sensitivity than conventional methods. Further, the present method can suppress generation of adduct ions to which an alkali metal such as sodium or potassium is added, and thus the peaks of those adduct ions do not appear in the mass spectrum. As a result, the peaks of the target phosphopeptide or other non-phosphopeptide can be more easily observed. Additionally, the method of the present invention enables detection of some peptides which are undetectable by conventional methods using a phosphoric acid as a matrix additive. Accordingly, failure of detection of peptides does not occur, and thus good sequence coverage is achieved in the identification of proteins for example by PMF, thereby improving the credibility of the analysis.

DETAILED DESCRIPTION OF A PREFERRED EMBODIMENT

Figure 1:
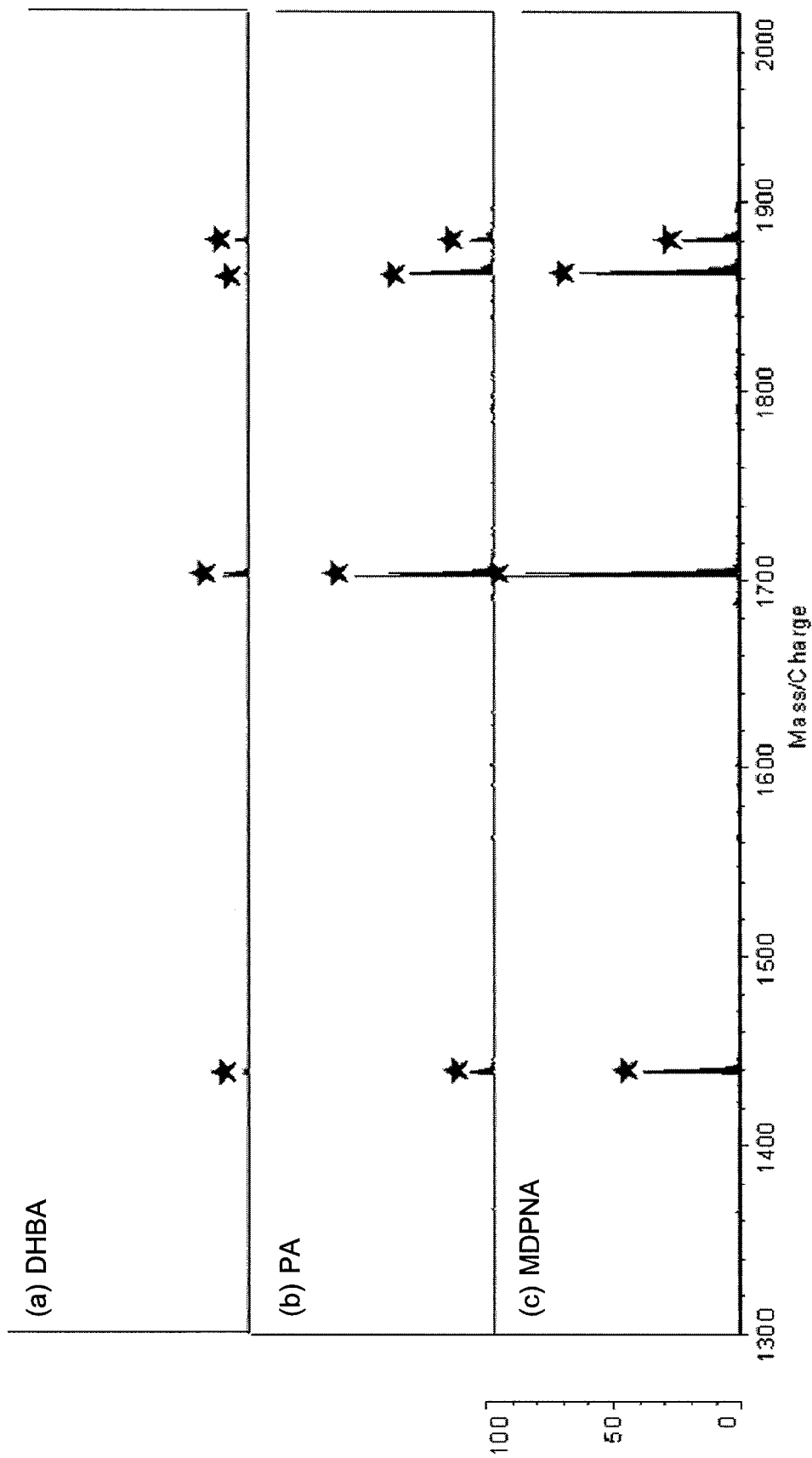
FIG. 1 is a diagram showing mass spectrums (positive ionization mode) of the mixed solutions of four kinds of peptides.

The method for analyzing phosphopeptide according to the present invention is performed as follows: a sample to be analyzed is prepared by using a matrix reagent to which a matrix additive having the specific characteristics mentioned later is added; the sample is placed on a sample plate for example made of a metal; the sample is analyzed by using a MALDI mass spectrometer such as a MALDI time-of-flight mass spectrometer to obtain a mass spectrum in a predetermined mass range; the peaks appearing in the mass spectrum are detected to obtain the mass-to-charge ratio or the peak intensity; and the qualitative determination or quantitative determination of the phosphopeptide is performed by making use of the obtained mass-to-charge ratio or the peak intensity.

EXAMPLES

The following description will discuss one embodiment of the method for analyzing phosphopeptide according to the present invention, by focusing on procedures and results of the tests that were carried out by the present inventors for comparison with the conventional methods.

[Test Procedures]

In the following test, a mass spectrum was measured by using a MALDI mass spectrometer "AXIMA-CFR" (manufactured by Shimadzu Corporation). The laser power of the MALDI ion source used in the test was appropriately optimized to obtain the most preferable spectrum in each matrix reagent. Further, the number of times for integrating the detection signals obtained by single laser irradiation was the same in all the cases.

The techniques and procedures for the preparation of the samples were common irrespective of the kind of matrix reagent. Namely, the matrix additive solution according to one embodiment of the present invention was prepared by dissolving 10 mg of methylenediphosphonic acid (MDPNA) in 1 mL of ultra pure water. On the other hand, phosphoric acid as a comparative matrix additive solution was diluted with ultra pure water to obtain a 3% (v/v) phosphoric acid solution. The matrix used in this example was a generally-used 2,5-dihydroxybenzoic acid (DHBA), prepared by dissolving 10 mg of 2,5-dihydroxybenzoic acid in 1 mL of 50% acetonitrile solution containing 0.05% trifluoroacetic acid (TFA). Collection of the sample on a sample plate was performed by dropping and mixing 0.3 µL each of the sample solution, the matrix additive solution (only when the matrix additive was used), and the matrix solution, in the order mentioned earlier. Thereafter, air-drying was performed.

1. Comparison of Detection Sensitivity

Four kinds of phosphopeptide described hereafter were used in the test. All of them were products of AnaSpec USA, and were listed in the peptide catalogue of the company.

(1) CaM Kinase II Substrate 281-291 phosphorylated (MMRQEpTVDCLK-NH$_2$, M+H, 1439.6); Here, the lower case letter "p" appearing in the sequences of the single letter symbols each showing an amino acid means that the residue immediately after the "p" was phosphorylated. Specifically, there are three kinds of "p", namely, pT, pS, and pY, which refer to phosphorylated threonine, phosphorylated serine, and phosphorylated tyrosine, respectively.

(2) Neurograin 28-43 phosphorylated (AAKIQApS-FRGHMARKK, M+H, 1881.2)

(3) Kinase Domain of Insulin Receptor phosphorylated 1142-1153 (TRDIpYETDYYRK, M+H, 1703.8)

(4) Kinase Domain of Insulin Receptor phosphorylated 1142-1153 (TRDIpYETDpYpYRK, M+H, 1863.8)

These four kinds of phosphopeptide were dissolved in ultra pure water so that a mixed solution containing 0.2 pmol/µL each of the phosphopeptide was prepared. The amount of the peptide collected on the sample plate was 60 fmol/well.

Figure 2:
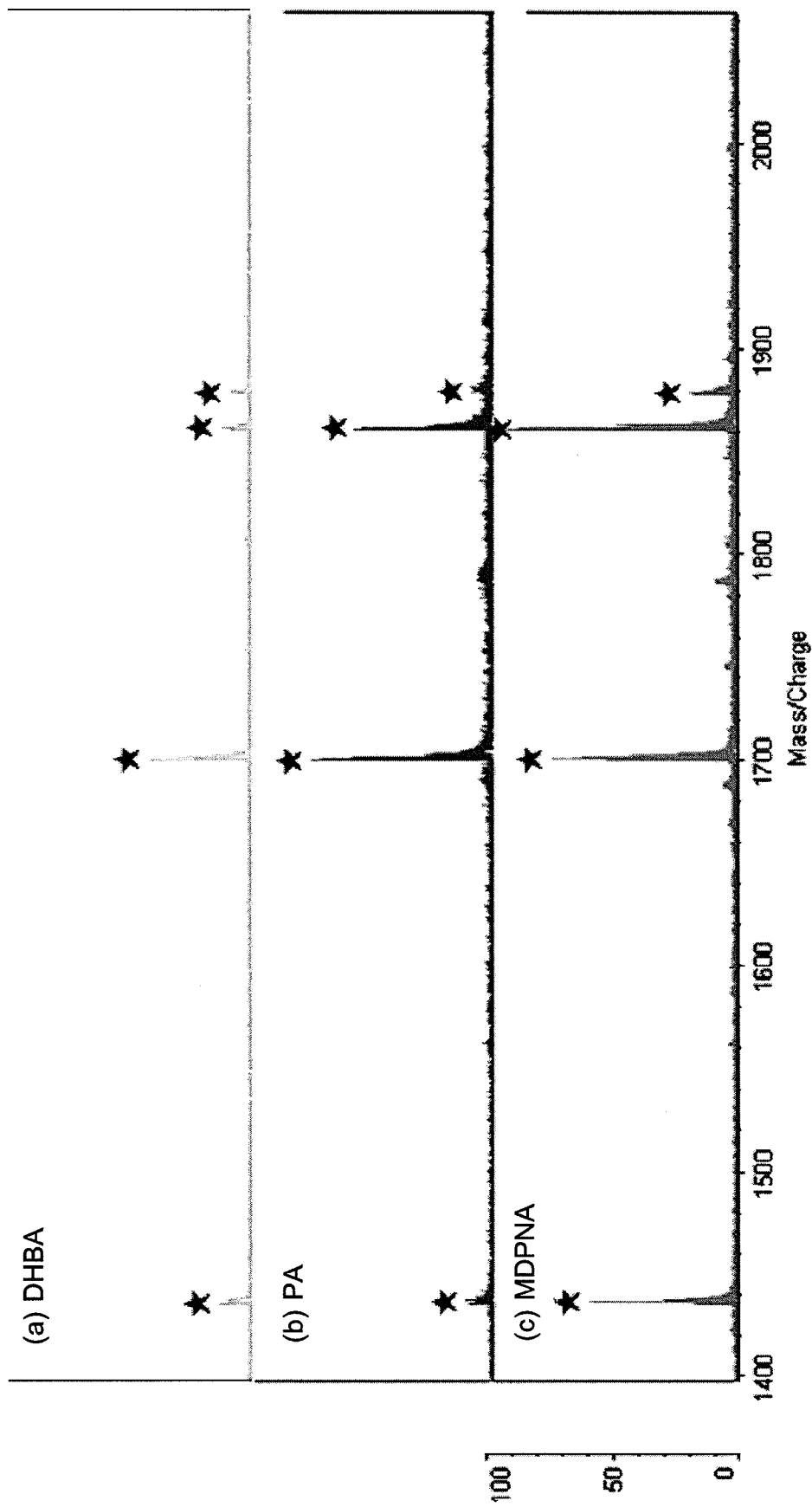
FIG. 2 is a diagram showing a mass spectrum (negative ionization mode) of the mixed solutions of four kinds of peptides.

FIG. 1 shows mass spectrums in a positive ionization mode generated by a MALDI mass spectrometer, and FIG. 2 shows mass spectrums in a negative ionization mode. In FIG. 1 and FIG. 2, the horizontal axis indicates a mass-to-charge ratio, and the vertical axis indicates a relative intensity of an ion. In order to facilitate comparison of signal intensities, the vertical axis scales of the mass spectrums were adjusted to correspond to the vertical axis scale of the mass spectrum (c) in both FIG. 1 and FIG. 2 (127 mV and 22 mV, respectively). The mass spectrum (a) is a mass spectrum of a peptide sample in which 2,5-dihydroxybenzoic acid was used as a matrix and no matrix additive was added; the mass spectrum (b) is a mass spectrum of a peptide sample in which 2,5-dihydroxybenzoic acid was used as a matrix and phosphoric acid (PA) was used as a matrix additive; and the mass spectrum (c) is a mass spectrum of a peptide sample in which 2,5-dihydroxybenzoic acid was used as a matrix and methylenediphosphonic acid (MDPNA) was used as a matrix additive. In other words, the mass spectrum (c) is a mass spectrum according to one embodiment of the present invention, and the mass spectrums (a) and (b) are those for the comparison test. In the drawings, the phosphopeptide peak was marked with a star symbol.

It was clearly found that, in both the positive ionization mode and the negative ionization mode, the peak intensities in the case (c) where methylenediphosphonic acid was used as a matrix additive were significantly higher than that in the case (a) where only 2,5-dihydroxybenzoic acid was used as a matrix without a matrix additive, or the case (b) where phosphoric acid was used as a matrix additive.

Table 1 and Table 2 show the peak intensities of each of the previously illustrated phosphopeptide (four kinds), with the peak intensities in the two cases (the case (b) and the case (c)) expressed as the relative value to the peak intensity in the case (a) where no matrix additive was used, given that the peak intensity in the case (a) is 1. A comparison between the sole use of 2,5-dihydroxybenzoic acid and the combination use of 2,5-dihydroxybenzoic acid with methylenediphosphonic acid reveals that the addition of methylenediphosphonic acid elevates the peak intensity by approximately 4 to 38 times in the positive ionization mode, and by approximately 2 to 8 times in the negative ionization mode, though the peak intensities are different among the peptides due to the influence of the structures (sequence). Also, a comparison between the addition of phosphoric acid and the addition of methylenediphosphonic acid revealed that the sensitivity was approximately 2 to 5 times higher in the methylenediphosphonic acid-addition case than the phosphoric acid-addition case.

TABLE 1

Positive ionization mode

| m/z | Peptide (1) 1493.6 | Peptide (3) 1703.8 | Peptide (4) 1863.8 | Peptide (2) 1881.2 |
|---|---|---|---|---|
| DHBA | 1 | 1 | 1 | 1 |
| PA added | 3.2 | 5.4 | 20.4 | 1.8 |
| MDPNA | 13.2 | 9.8 | 38.6 | 4.3 |

TABLE 2

Negative ionization mode

| m/z | Peptide (1) 1493.6 | Peptide (3) 1703.8 | Peptide (4) 1863.8 | Peptide (2) 1881.2 |
|---|---|---|---|---|
| DHBA | 1 | 1 | 1 | 1 |
| PA added | 0.9 | 1.8 | 4.4 | 1 |
| MDPNA | 4.5 | 1.8 | 8.1 | 2.1 |

2. Confirmation of Suppressing Effects on Alkali Metal (Na, K)-Adduct Ion Generation The following six kinds of peptides were used in the test.

(1) WAGGDASGR       (M + H: 848.8)
(2) WAGGDApSGR      (M + H: 928.8)
(3) GFETVPETG-NH$_2$   (M + H: 935.4)
(4) GFETVPEpTG-NH$_2$  (M + H: 1015.4)
(5) TSTEPQYQPGENL   (M + H: 1463.5)
(6) TSTEPQpYQPGENL  (M + H: 1543.5)

Figure 3:
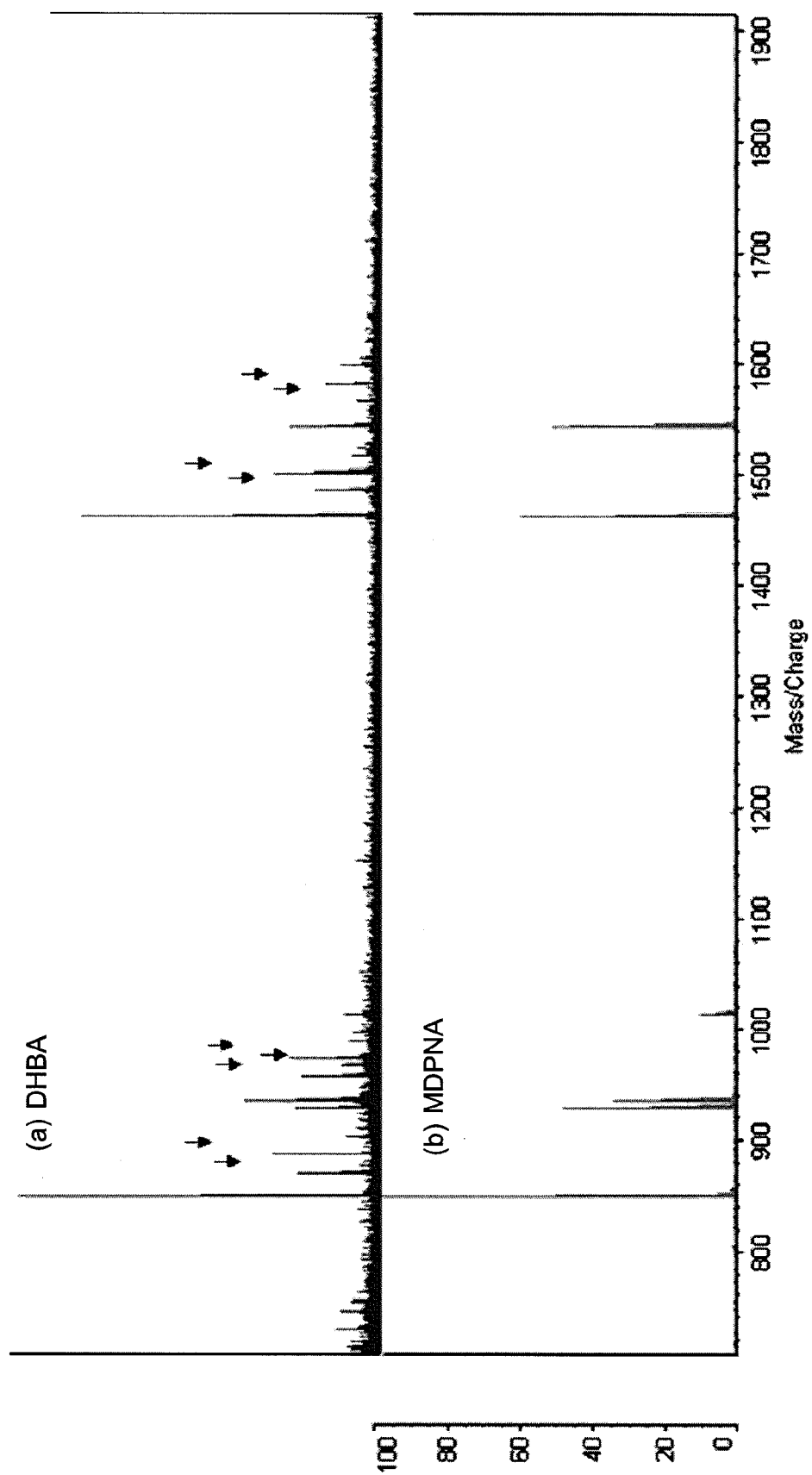
FIG. 3 is a diagram showing mass spectrums for examining the suppressing effect on alkali metal-adduct ions.

The six kinds of peptides were dissolved in 0.1% trifluoroacetic acid (TFA) solution serving as a solvent so that a mixed solution containing 1.7 pmol/μL each of the peptides was prepared. The amount of the peptide collected on a sample plate was 0.5 pmol/well and 0.3 μL in total for each of the peptides. FIG. 3 shows mass spectrums generated by a MALDI mass spectrometer in this test. The mass spectrum (a) is a mass spectrum of a peptide sample in which 2,5-dihydroxybenzoic acid was used as a matrix and no matrix additive was added; and the mass spectrum (b) is a mass spectrum of a peptide sample in which 2,5-dihydroxybenzoic acid was used as a matrix and methylenediphosphonic acid was used as a matrix additive. In FIG. 3, peaks of Na-adduct ions and K-adduct ions are marked with downward arrows.

In FIG. 3(a), the peaks of alkali metals (Na, K)-adduct ions appeared in the mass spectrums of all the peptides except for the peptide (4), making the spectrums complicated, while in FIG. (b), no peaks of the adduct ions were observed in the mass spectrums of all the peptides. It was thus found that generation of the adduct ions can be suppressed when methylenediphosphonic acid was used as a matrix additive.

3. Comparison of Lower Limit of Detectable Concentration

Figure 4:
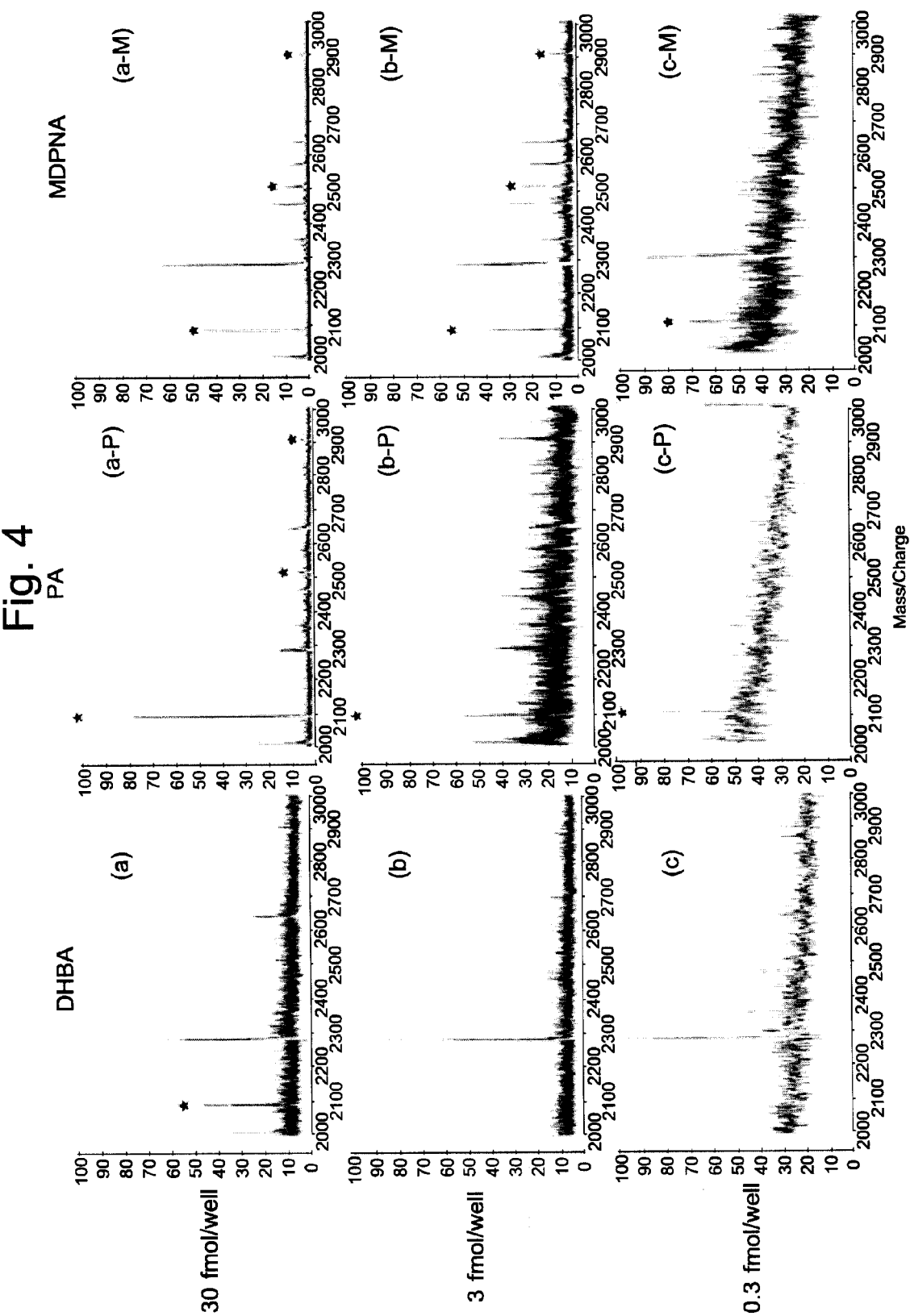
FIG. 4 is a diagram showing mass spectrums for determining a lower limit of phosphopeptide detection.

A trypsin-digested ovalbumin was used as a sample. After reduction and alkylation of ovalbumin according to a common method, the resulting product was treated in a digestive buffer (50 mM Tris-HCl, 5 mM CaCl$_2$, trypsin 20 μg/mL, pH 7.8) for 12 hours at a temperature of 37° C. The solution of the digested product obtained above was diluted with a 50% acetonitrile solution containing a 0.05% trifluoroacetic acid so as to prepare a sample solution. The sample solution was collected in wells of a sample plate with three kinds of concentration of 30 fmol, 3 fmol, and 0.3 fmol, and then the detection sensitivity was compared among them. FIG. 4 shows mass spectrums generated by a MALDI mass spectrometer in this test, and the mass spectrums (a), (b), and (c) correspond to the concentrations 30 fmol, 3 fmol, and 0.3 fmol, respectively, and the spectrums (x-P) and (x-M) (in which x is a, b, or c) show the results of the cases where the matrix additive used were phosphoric acid and methylenediphosphonic acid, respectively.

The phosphopeptide in the theoretical digested fragments of ovalbumin were the following three kinds:

(1) EVVGpSAEAGVDAASVSEEFR     (M + H: 2088.9);
(2) LPGFGDpSIEAQCGTSVNVHSSLR  (M + H: 2511.1); and
(3) FDKLPGFGDSIEAQCGTSVNVHSSLR (M + H: 2901.3).

In FIG. 4, the peaks of those peptides are marked with a star symbol. In the spectrums of the highest concentration of 30 fmol, only one kind of the phosphopeptide contained in the three kinds of theoretical digested fragments was observed when 2,5-dihydroxybenzoic acid was solely used (case a); and all three kinds of phosphopeptide were observed when phosphoric acid (case a-P) or methylenediphosphonic acid (case a-M) was further added. In the spectrums of the lower concentration of 3 fmol, no peak of the phosphopeptide was observed when 2,5-dihydroxybenzoic acid was solely used (case b); a peak of only one kind of the phosphopeptide was observed when phosphoric acid was added (case b-P); while peaks of all three kinds of the phosphopeptide were observed when methylenediphosphonic acid was added (case b-M), among the three kinds of theoretical digested fragments. On the other hand, in the spectrums of the lowest concentration of 0.3 fmol, peaks of only one kind of the phosphopeptide were observed when phosphoric acid (case c-P) or methylenediphosphonic acid (case c-M) was further added. It has been found from those results that the addition of methylenediphosphonic acid elevates the sensitivity by approximately 100 times as compared with the sole use of 2,5-dihydroxybenzoic acid, and by approximately 10 times as compared with the addition of phosphoric acid, though the detection sensitivities are different among the phosphopeptide due to the influence of peptide structures (sequence) or other factors.

4. Comparison with Addition of Phosphoric Acid Concerning Undetectable Peptides

A trypsin-digested product as a sample was prepared by the following procedures. Namely, 100 μg of α-casein was dissolved in 0.5 mL of a digestive buffer (50 mM Tris-HCl, 5 mM $CaCl_2$, trypsin 20 μg/mL, pH 7.8) and treated for 12 hours at a temperature of 37° C. The resulting solution of the digested product was diluted with a 50% acetonitrile solution containing 0.05% trifluoroacetic acid to have a concentration of 1 pmol/μL so that a sample solution was prepared. The amount of the sample solution collected in wells of a sample plate was 300 fmol/well.

The theoretical digested fragments of α-casein in the range of m/z 600 to 1000 were the following six kinds:

| (1) | LHSMK | (M + H: 615.3) |
|---|---|---|
| (2) | VNELSK | (M + H: 689.4) |
| (3) | TTMPLW | (M + H: 748.4) |
| (4) | VNELpSK | (M + H: 769.3) |
| (5) | EDVPSER | (M + H: 831.4) |
| (6) | EGIHAQQK | (M + H: 910.5) |

Figure 5:
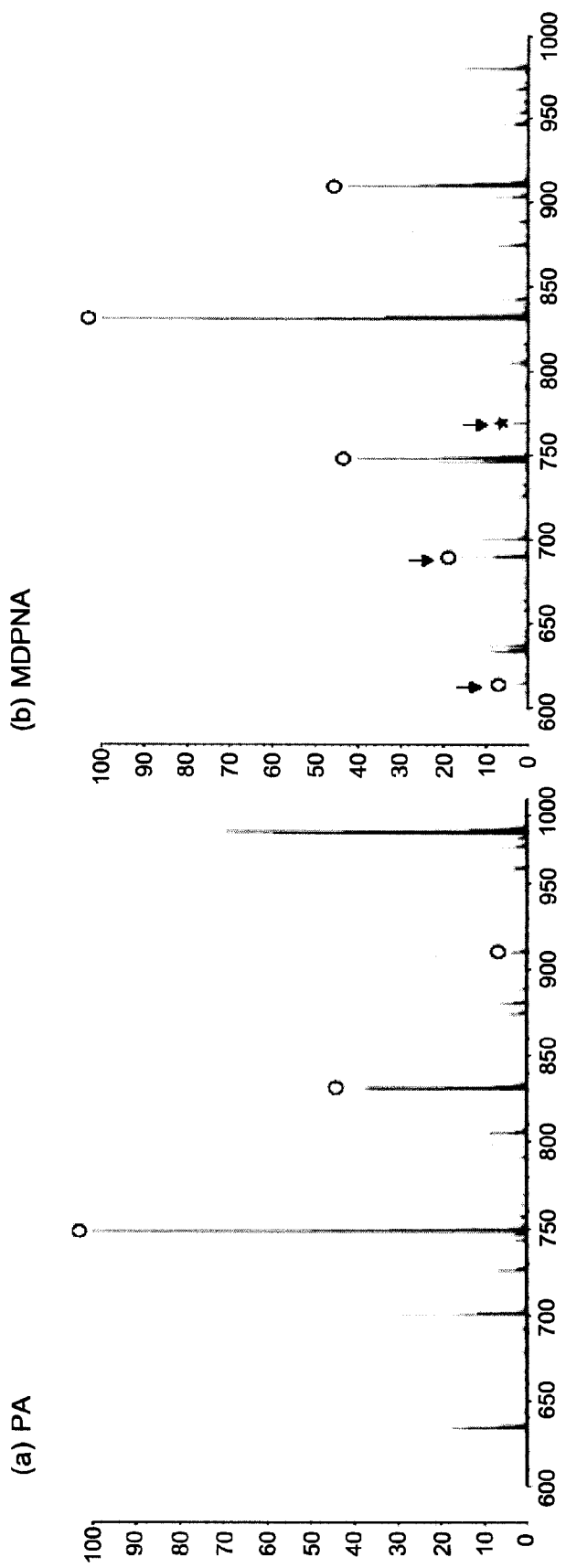
FIG. 5 is a diagram showing mass spectrums for determining differences in undetectable peptides.

FIG. 5 shows mass spectrums generated by a MALDI mass spectrometer in this test. FIG. 5(a) is a spectrum obtained when phosphoric acid was added, and FIG. 5(b) is a spectrum obtained when methylenediphosphonic acid was added. In the drawings, the peak of the phosphopeptide derived from an α-casein digested product is marked with a star symbol, and the peaks of the non-phosphopeptide derived from an α-casein digested product are marked with a circle symbol. The results show that all six kinds of the peptide fragments to be detected were observed when methylenediphosphonic acid was added. On the other hand, undetectable peptides were present when phosphoric acid was added. Specifically, the three kinds of peptide fragments (1), (2), and (4), which were marked with downward arrows, were not detected. It is to be noted that the peptide fragments (1) and (2) were non-phosphorylated peptides, and the peptide fragment (4) was a phosphorylated peptide. This result shows that the use of methylenediphosphonic acid as a matrix additive can prevent the failure of detection of the peptides from occurring.

By summarizing the above test results, it is confirmed that use of the matrix reagent containing methylenediphosphonic acid as a matrix additive and 2,5-dihydroxybenzoic acid as a matrix, according to one embodiment of the present invention in preparation of a sample can improve the phosphopeptide-detection sensitivity and can suppress the generation of alkali metal-adduct ions, as compared with the conventional techniques. Further, the method of the present invention enables detection of the peptides which are undetectable by conventional methods.

Although, the previous embodiment detailed the test results obtained when using the methylenediphosphonic acid containing two phosphonic acid groups as a matrix additive, it has also been confirmed that almost the same effects can be achieved when using other compounds containing two or more phosphonic acid groups, specifically such as ethylenediphosphonic acid, ethane-1-hydroxy-1,1-diphosphonic acid, and ethylenediaminotetraphosphonic acid.

It is to be noted that the previous example is just one example of the present invention, and an appropriate change, modification, and addition can certainly be applied thereto within the scope of the present invention.

What is claimed is:

1. A method for analyzing phophopeptide, comprising: first, adding a compound containing a phosphonic acid group to a matrix used in a matrix assisted laser desorption ionization (MALDI) mass spectrometer, and second, analyzing phosphopeptide using MALDI; wherein the compound containing a phosphonic acid group includes not less than two phosphonic acid groups in one molecule.

2. The method for analyzing phosphopeptide according to claim 1, wherein the matrix is 2,5-dihydroxybenzoic acid (DHBA).

3. The method for analyzing phosphopeptide according to claim 1, wherein the compound containing a phosphonic acid group is methylenediphosphonic acid.

4. The method for analyzing phosphopeptide according to claim 1, wherein the compound containing a phosphonic acid group includes two to four phosphonic acid groups in one molecule.

5. The method for analyzing phosphopeptide according to claim 1, wherein a content of the matrix additive in a matrix additive solution is in the range from 1 to 5% (w/v).

* * * * *